US010667836B2

(12) United States Patent
Fojtik et al.

(10) Patent No.: US 10,667,836 B2
(45) Date of Patent: *Jun. 2, 2020

(54) TISSUE RESECTORS, HAND OPERATED TISSUE RESECTING SYSTEMS, AND ASSOCIATED METHODS

(71) Applicant: BOSTON SCIENTIFIC SCIMED, INC., Maple Grove, MN (US)

(72) Inventors: Shawn P. Fojtik, Park City, UT (US); Annette Lavoie, Park City, UT (US); Timothy R. Nieman, North Salt Lake, UT (US); Erik S. Liddiard, West Jordan, UT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 571 days.

This patent is subject to a terminal disclaimer.

(21) Appl. No.: 15/285,479

(22) Filed: Oct. 4, 2016

(65) Prior Publication Data

US 2017/0189046 A1    Jul. 6, 2017

Related U.S. Application Data

(63) Continuation-in-part of application No. 14/698,743, filed on Apr. 28, 2015, now Pat. No. 10,376,278.
(Continued)

(51) Int. Cl.
*A61B 17/32* (2006.01)
*A61B 17/3205* (2006.01)
(Continued)

(52) U.S. Cl.
CPC .............. *A61B 17/32002* (2013.01); *A61B 17/320016* (2013.01); *A61B 17/32053* (2013.01);
(Continued)

(58) Field of Classification Search
CPC .. A61B 17/32002; A61B 2017/320024; A61B 2017/320032; A61B 2017/320775;
(Continued)

(56) References Cited

U.S. PATENT DOCUMENTS

| 4,850,957 A | 7/1989 | Summers |
| 5,498,258 A | 3/1996 | Hakky et al. |

(Continued)

FOREIGN PATENT DOCUMENTS

WO    9611638 A1    4/1996

OTHER PUBLICATIONS

International Search Report and Written Opinion dated Dec. 22, 2017 for International Application No. PCT/US2017/054871.

*Primary Examiner* — Diane D Yabut
(74) *Attorney, Agent, or Firm* — Seager, Tufte & Wickhem, LLP (57) ABSTRACT

A tissue resector includes an outer cannula with a cutting element disposed therein. The outer cannula includes an opening that is configured to be associated with a cutting element of the cutting element in such a way that when tissue is drawn into the opening of the cannula, a cutting element of the cutting element can be rotated past the opening to engage and cut into and through the tissue. The outer cannula and the cutting element may also be configured to enable aspiration of the tissue. A tissue resector according to this disclosure may be used with a hand-held, hand-operated rooter.

17 Claims, 7 Drawing Sheets

Related U.S. Application Data

(60) Provisional application No. 61/985,283, filed on Apr. 28, 2014.

(51) Int. Cl.
  *A61B 17/3207* (2006.01)
  *A61B 17/42* (2006.01)

(52) U.S. Cl.
  CPC ............ *A61B 17/320758* (2013.01); *A61B 2017/320024* (2013.01); *A61B 2017/320032* (2013.01); *A61B 2017/320775* (2013.01); *A61B 2017/4216* (2013.01); *A61B 2217/005* (2013.01)

(58) Field of Classification Search
  CPC ...... A61B 2017/4216; A61B 2217/005; A61B 17/320016; A61B 17/320758; A61B 17/320783; A61B 17/22; A61B 2017/320791; A61B 2017/320766
  See application file for complete search history.

(56) References Cited

U.S. PATENT DOCUMENTS

| | | |
|---|---|---|
| 5,591,187 A | 1/1997 | Dekel |
| 6,251,120 B1 | 6/2001 | Dorn |
| 2012/0239008 A1 | 9/2012 | Fojtik |
| 2015/0305765 A1 | 10/2015 | Fojtik et al. |

TISSUE RESECTORS, HAND OPERATED TISSUE RESECTING SYSTEMS, AND ASSOCIATED METHODS

CROSS-REFERENCE TO RELATED APPLICATION

This application is a continuation-in-part of U.S. patent application Ser. No. 14/698,743, filed on Apr. 28, 2015, now U.S. Pat. No. 10,376,278, and titled TISSUE RESECTORS WITH CUTTING ELEMENTS, HAND-OPERATED TISSUE RESECTING SYSTEMS AND ASSOCIATED METHODS ("the '743 Application"). A claim to the benefit of the Apr. 28, 2014 filing date of U.S. Provisional Patent Application No. 61/985,283, titled MORCELLATORS WITH CUTTING ELEMENTS, HAND-OPERATED MORCELLATION SYSTEMS AND ASSOCIATED METHODS ("the '283 Provisional Application") was made in the '743 Application pursuant to 35 U.S.C. § 119(e). The entire disclosures of the '743 Application and the '283 Provisional Application are hereby incorporated by reference.

TECHNICAL FIELD

This disclosure relates generally to tissue resectors and, more specifically, to tissue resectors that efficiently aspirate excised tissue. In particular, tissue resectors that employ wires to remove undesired tissue, such as benign tumors, polyps, and fibroids, are disclosed. Systems and methods for resecting tissue are also disclosed.

RELATED ART

Tissue resection is a process by which undesirable growths, such as benign tumors, polyps and fibroids, are removed from within a subject's body. Removal of benign tumors, polyps, and fibroids from a female's uterus may be conducted in conjunction with a hysteroscope, which enables the physician to visualize the inside of the uterus. Small tissue resectors have been used in conjunction with hysteroscopes to remove relatively small uterine polyps (e.g., polyps with diameters of about 3 cm or less, etc.) and fibroids (which typically have diameters of about 1 cm to about 2 cm). Some hysteroscopes are configured to inflate the uterine cavity with fluid or air. With the uterine cavity inflated, a light source of the hysteroscope may illuminate the interior surfaces of the uterus, and a camera of the hysterscope and a display associated with the camera of the hysteroscope may enable a physician to visualize features, such as polyps and fibroids, on interior surfaces of the uterus. While the physician is looking at the interior surface of the uterine wall, he or she may operate a small tissue resector in conjunction with the hysteroscope to remove any polyps or fibroids that appear on the display. Debris from the tissue resection process may be aspirated through the small tissue resector, and collected for pathology. Currently, about 11 million uterine polyp and small fibroid resection procedures are performed annually throughout the world.

Physicians have also used tissue resection processes to laparoscopically remove large masses of tissues—a process that is sometimes referred to as "morcellation." Morcellation is used in laparoscopic gynecological surgeries. For example, high powered electric morcellators have been used to laparoscopically extract the uterus (i.e., hysterectomy). Specifically, an electric morcellator grinds the entire uterus, including any undiagnosed sarcomas. While the risk is relatively small that these cancerous tissues remain within a woman's body, there is a significant likelihood that any cancerous cells that remain within the body may spread.

The morcellators that are currently used to remove uterine polyps and fibroids are power-driven devices. A typical morcellator includes an outer cannula with an opening located near its distal end and formed in a portion of the circumference of the outer cannula. An inner cannula is positioned within a lumen of the outer cannula, and includes a distal end that defines and blade that communicates with the opening near the distal end of the outer cannula. Depending upon the configurations of the opening and the blade, the inner cannula may rotate within the lumen of the outer cannula, or the inner cannula may move longitudinally back and forth within the outer cannula. In any configuration, a polyp or fibroid may be drawn into the opening in the outer cannula, and then cut with the blade of the inner cannula. Once the polyp or fibroid, or a portion thereof, has been cut from the inner surface of the uterus, it may be drawn, by way of a vacuum, through a lumen in the inner cannula.

One example of an existing morcellator is the TRUCLEAR® morcellator offered by Smith & Nephew. That morcellator includes an outer cannula that has an outer diameter of 0.114 inch (i.e., a cross-sectional area of 0.0102 $in^2$) and an inner cannula with an inner diameter of about 0.070 inch (i.e., a cross-sectional area of 0.00385 $in^2$). Thus, the available, open cross-sectional area through that device only comprises 37.7% of the overall cross-sectional area occupied by the cannula of that device.

Hysteroscopy and tissue resection can be painful. The relatively small inner diameters of the inner cannulas of existing tissue resectors limit the rates at which excised tissues (e.g., polyps, fibroids, etc.) may be collected, which unfortunately and undesirably prolongs the tissue resection procedure and the pain caused by that procedure.

Tissue resection procedures may also be used to remove benign tumors, polyps, and other growths from other locations within a subject's body. As an example, tissue resection procedures may also be used to remove nasal polyps. The PolypVac microdebrider available from Laurimed, LLC, of Redwood City, Calif., is an example of an electromechanically operated device with a flexible tip that can be used to perform such a procedure.

SUMMARY

A tissue resector according to this disclosure includes a cannula and a cutting element. The cannula has a lumen within which the cutting element may be positioned. The cannula includes an opening located at or adjacent to its distal end. The opening may be configured to receive uterine polyps and fibroids. A cutting feature at or near a distal end of the cutting element cooperates with the opening of the cannula in such a way that the cutting feature will cut, slice, shear, chew, or tear tissue that is introduced (e.g., by suction, etc.) into the opening. For the sake of simplicity, the acts of cutting, slicing, shearing, chewing, tearing, and similar actions are individually and collectively referred to herein as "cutting."

In addition to the cutting feature, the cutting element may include a drive feature. The drive feature may comprise a wire. The cutting feature of the cutting element may be formed at a distal end of the drive feature, or the cutting feature may be secured (e.g., welded, etc.) to the distal end of the drive feature. Embodiments where the drive feature comprises a wire may be referred to as "single-cannula" tissue resectors.

The use of a wire as the drive feature of the cutting element within the cannula may provide for a relatively large cross-sectional area through which tissue may be aspirated through the cannula. In various embodiments, of the entire cross-sectional area occupied by the cannula, at least 50% may be available for aspiration. In some embodiments (e.g., embodiments where cutting elements with smaller drive features, such as wires, are used, etc.), the open area may comprise 60%, or even 70% of the entire cross-sectional area occupied by the cannula.

In another aspect of this disclosure, a tissue resector may be part of a tissue resector system. In some embodiments, the tissue resector may be used with a rooter that operates under manual power, such as that disclosed by U.S. Patent Application Publication No. US 2012/0239008 of Fojtik, the entire disclosure of which is hereby incorporated herein. Such a rooter is also referred to herein as a "hand-powered rooter" and as a "manual spinning instrument." In other embodiments, the tissue resector may be used with a power-driven instrument, such as those used to drive the inner cannulas of existing morcellators, and an appropriate adapter, which translates actions of the power-driven instrument to the features of a tissue resector with a single cannula and a cutting element.

Another embodiment of tissue resector system includes an existing resector blade (with an outer cannula and an inner cannula on which a blade is defined), a hand-operated rooter and an adapter for converting actions of the rooter to the features of existing resector blade.

As an example of use, a tissue resector or tissue resector system according to this disclosure may be used for a variety of purposes. For example, a tissue resector or a tissue resector system may be used to remove any type of tissue. In a specific embodiment, a tissue resector or a tissue resector system may be used to remove undesired growths from a woman's uterus, including, without limitation, polyps, fibroids, and other undesirable growths. In some other embodiments, a tissue resector or a tissue resector system may be used in atheectromy procedures (i.e., the removal of athromas and blood clots from the insides of blood vessels), in soft tissue biopsy procedures, in tumor removal procedures, in trans ureter retrograde prostate resection procedures, in liposuction procedures, in procedures for treating carpal tunnel syndrome, in procedures for shaving protrusions from ligaments, tendons, and/or bones, and in a variety of other procedures in which tissue is removed from a subject's body. While viewing the tissue to be resected, that tissue may be drawn into the opening of a cannula under suction (i.e., a vacuum) applied to the lumen of the cannula. With the tissue in the opening, the cutting element may be rotated, and its cutting feature may cut tissue from the growth. This process may continue until the growth and immediately adjacent tissues have been removed. The tissues, which are aspirated, may then be collected and evaluated by a pathologist.

Other aspects, as well as features and advantages of various aspects, of the disclosed subject matter will become apparent to those of ordinary skill in the art through consideration of the ensuing description, the accompanying drawings and the appended claims.

DETAILED DESCRIPTION

Figure 1A:
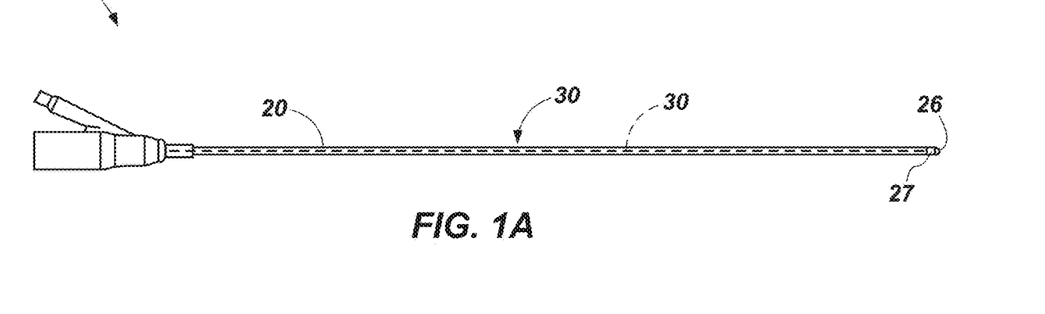
FIGS. 1A and 1B depict an embodiment of a tissue resector that includes a cannula and a cutting element within a lumen of the cannula.
Figures 1B, 2A, 2B:
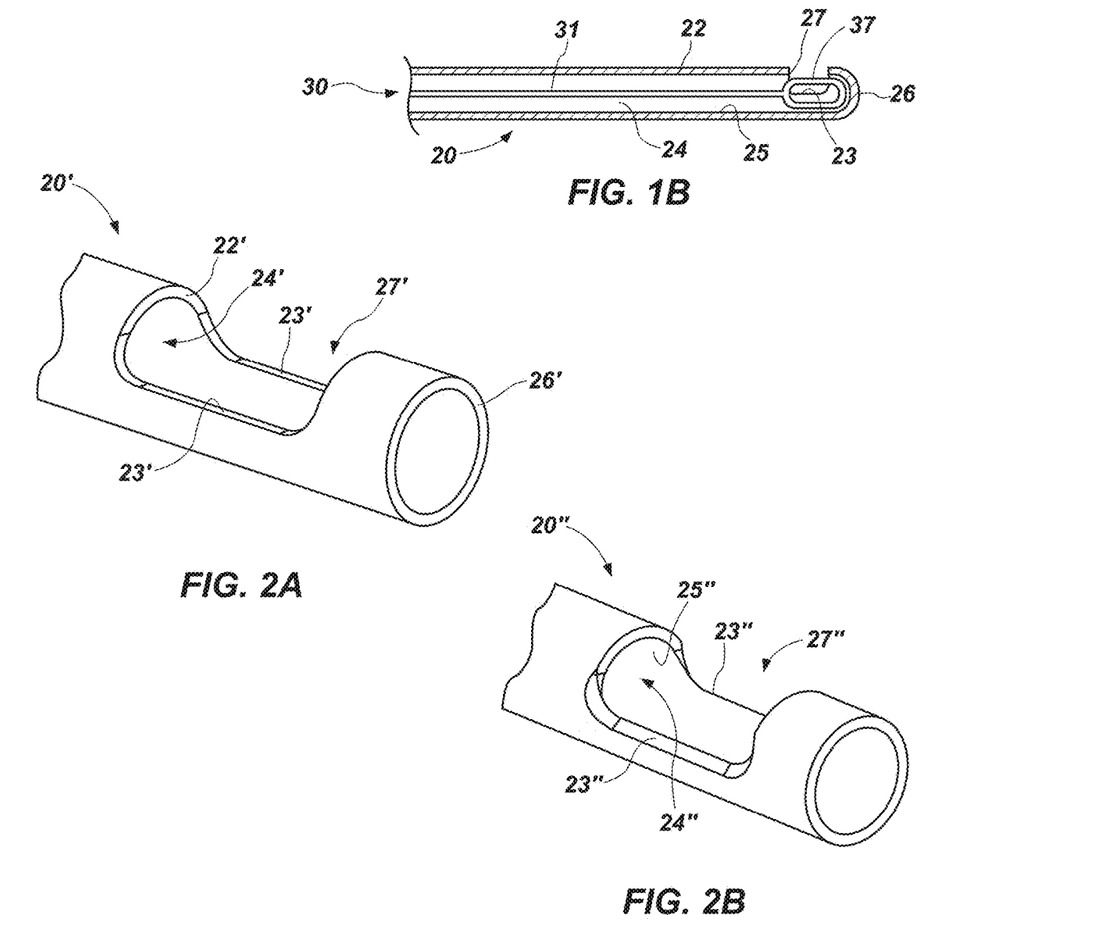
FIGS. 2A through 2G depict various embodiments of distal ends of and openings of the cannulas of various embodiments of tissue resectors that incorporate the features shown in FIGS. 1A and 1B.

As shown in FIGS. 1A and 1B, a tissue resector 10 according to this disclosure includes a cannula 20 and a cutting element 30. The cutting element 30 includes a drive feature 31 and a cutting feature 37. The drive feature may be flexible (e.g., it may comprise a wire, etc.). The cannula 20 is an elongated tubular element with a wall 22 that defines a lumen 24 along its length. In the illustrated embodiment, the cannula 20 is substantially straight; however, embodiments of tissue resectors 10 according to this disclosure that include cutting elements 30 with flexible drive features 31 may include curved cannulas 20 or bent cannulas 20, as a flexible drive feature 31 may rotate the cutting feature 32 even when the drive feature 31 is curved or bent.

The cannula 20 of a tissue resector 10 may have any of a variety of different dimensions. Without limitation, a cannula 20 may have an outer diameter of about 5 French (i.e., 0.066 inch; 1.67 mm), about 7 French (i.e., 0.092 inch; 2.33 mm) or about 9 French (i.e., 0.118 inch; 3 mm), which may correspond to the size of a hysteroscope (e.g., to the size of an access lumen through the hysteroscope, etc.) with which the tissue resector 10 is to be used. In a specific embodiment, the cannula 20 may comprise a hypotube with an outer diameter of 0.115 inch and an inner diameter of 0.095 inch.

The cannula 20 may have any suitable length. As an example, the cannula 20 of a tissue resector 10 that is configured to be inserted into a cavity, internal location, or vessel of a subject's body may be about 35 cm long (e.g., 34 cm long, etc.) or longer. A cannula 20 that is configured for use on exposed surfaces (e.g., to biopsy exposed tissue (e.g., tissue that is readily accessible from outside a subject's body, tissue that has been exposed by a surgical procedure, etc.), remove a tumor, remove tissue protruding from a ligament, a tendon, or a bone, etc.) may be much shorter; for example, about 5 cm in length or shorter.

At or near its distal end 26, the cannula 20 includes an opening 27. The opening 27 is configured to receive tissue (e.g., soft tissue, undesirable growths, such as uterine polyps and fibroids, soft tissue to be biopsied, a tumor, a portion of a ligament, a tendon, or a bone, etc.). In some embodiments, the edges 23 of the outer wall 22 that define the opening 27 may be configured to facilitate separation of the tissue that is to be removed (e.g., unwanted tissue, etc.) from adjacent tissue (e.g., healthy, etc.). A size of the opening 27 may depend on a particular use for which the cannula 20 and the tissue resector 10 are configured. Without limitation, the opening 27 may have a length of about 5 mm, a length of about 7.5 mm or any other suitable length.

FIGS. 2A through 2G illustrate various embodiments of openings 27 in the cannula 20 or a tissue resector 10.

The cannula 20' depicted by FIG. 2A includes an opening 27' through its wall 22' and positioned proximal to the distal end 26' of the cannula 20'. This configuration retains the tubularity of distal-most portion of the cannula 20', which may hold a distal end of a cutting element 30 (FIGS. 1A and 1B) in place as the cutting element 30 is rotated within the lumen 24' of the cannula 20'. The opening 27' has a width that is about the same as a diameter of the cannula 20', and is at least partially defined by edges 23' that are oriented longitudinally relative to the length of the cannula 20'. The opening 27' is elongated, with its length being oriented along the length of the cannula 20'.

FIG. 2B depicts an embodiment of a cannula 20" that includes an opening 27" with a position and a configuration similar to those of the opening 27' of the embodiment of cannula 20' depicted by FIG. 2A. However, the edges 23" that define the periphery of the opening 27" are configured as blades, with sharper edges adjacent to an interior surface 25" of the lumen 24" than the corresponding edges 23' that define the opening 27' of cannula 20'. Thus, the edges 23" that define the opening 27" may cut into tissue as a cutting element 30 (FIGS. 1A and 1B) rotates within the lumen 24" that extends through the cannula 20".

Figure 2C:
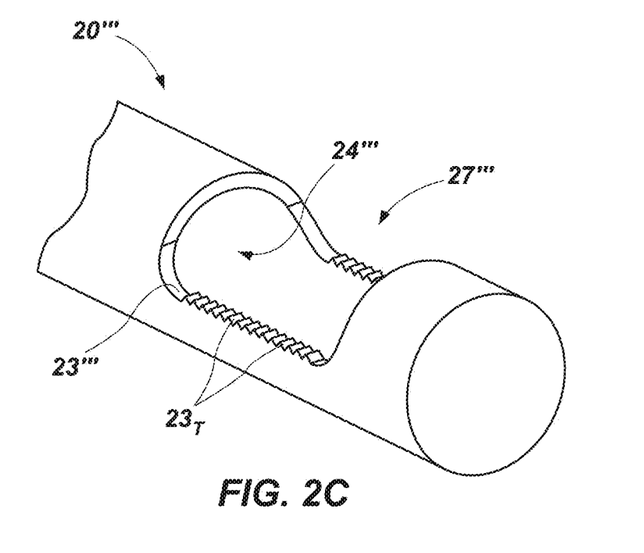

Another similarly positioned and configured opening 27''' is depicted by FIG. 2C, but with edges 23''' that include teeth 23$_T$. The teeth 23$_T$ may be configured to cut into tissue as a cutting element 30 (FIGS. 1A and 1B) rotates within the lumen 24''' that extends through the cannula 20'''.

Figure 2D:
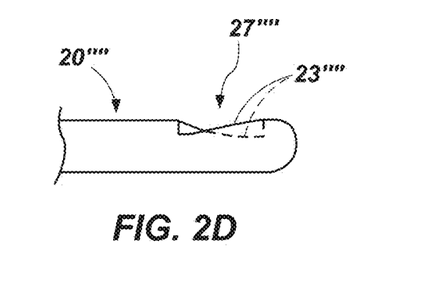

The embodiment of tissue resector 10'''' illustrated by FIG. 2D includes a cannula 20'''' with an opening 27'''' that is at least partially defined by edges 23'''' that are oriented oblique to the length, or longitudinal axis, of the cannula 20''''.

Figure 2E:
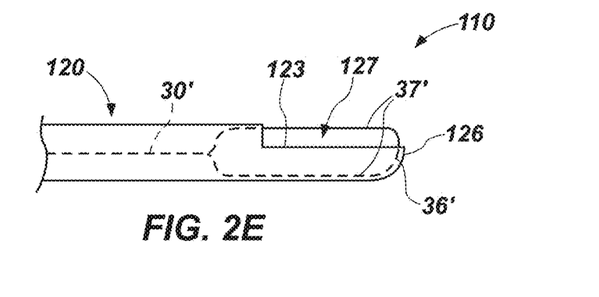

In FIG. 2E an embodiment of tissue resector 110 is shown with an opening 127 that extends to the distal end 126 of the cannula 120. In that embodiment, the portion of the distal end 126 that remains is closed. Such a configuration may be used with a cutting element 30' that has a cutting loop 37' at its distal end 36', and may at least partially hold the distal end 36' in place as the cutting element 30' rotates. The edges 123 that define the opening 127 may have any configuration, including, but not limited to, a substantially square configuration, or any of the configurations shown in and described in reference to FIGS. 2B through 2D.

Figure 2F:
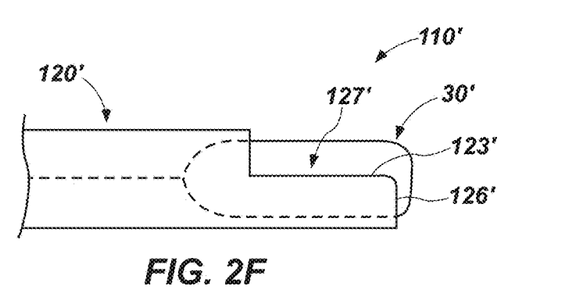

The embodiment of tissue resector 110' shown in FIG. 2F includes a cannula 120' with an opening 127' similar in configuration to the opening 127 of the embodiment of cannula 120 depicted by FIG. 2E; however, the entire distal end 126' of the cannula 120' is open. The edges 123' that define the opening 127' may have any configuration, including, but not limited to, a substantially square configuration, or any of the configurations shown in and described in reference to FIGS. 2B through 2D.

Figure 2G:
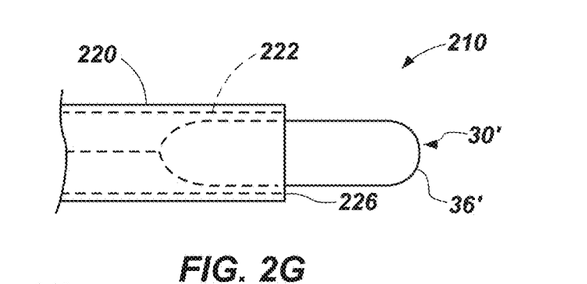

In the embodiment of tissue resector 210 depicted by FIG. 2G, the cannula 220 includes an open distal end 226, but no opening that extends into any portion of the circumference (i.e., the wall 222) of the cannula 220. The distal end 36' of a cutting element 30', which may be configured (e.g., with a loop, etc.) to cut or otherwise separate tissues that are drawn into or otherwise come into contact with the distal end 226 of the cannula 220, may protrude distally beyond the distal end 226 of the cannula 220.

Figure 3A:
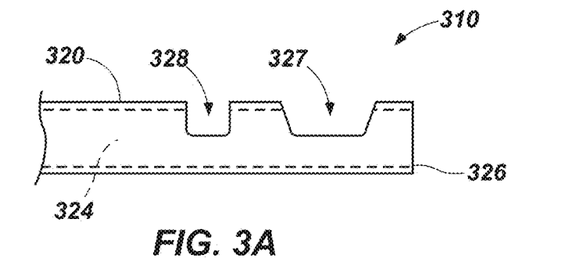
FIGS. 3A and 3B illustrate some embodiments of cannulas that include two or more openings.
Figure 3B:
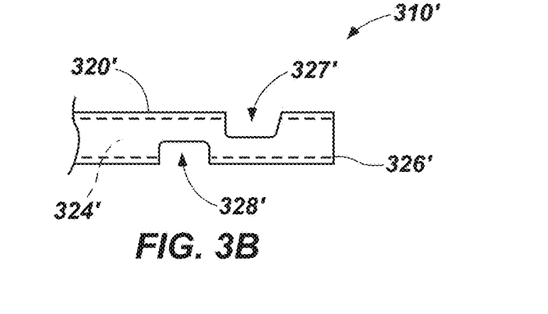

In some embodiments, such as those depicted by FIGS. 3A and 3B, the cannula 320, 320' of a tissue resector 310, 310' may include at least one additional opening 328, 328'. Such an opening 328, 328' may tailor the manner in which debris is aspirated through the lumen 324, 324' of the cannula 320, 320' (e.g., by balancing suction, etc.), or it may provide another location (i.e., in addition to the opening 327, 327' located closer to the distal end 326, 326' of the cannula 320, 320') at which an undesired growth, such as a uterine polyp or fibroid, may be engaged, severed and aspirated by the tissue resector 310, 310'. In the embodiment depicted by FIG. 3A, the opening 328 is longitudinally aligned with and located proximal to the opening 327, but is smaller than the opening 327. FIG. 3B shows an embodiment in which the openings 327 and 328 are located on different sides, or at different locations around the circumference, of the cannula 320.

While FIGS. 2A through 2F respectively show embodiments of cannulas with openings that are that are at least partially defined by edges that are linear or substantially linear, and, with the exception of the embodiment depicted by FIG. 2D, are oriented substantially parallel to the lengths of their respective cannulas, the edges that define the openings through the illustrated cannulas or any other embodiments of cannulas may be curved, may include curved sections and/or may be oriented at oblique angles to their respective cannulas.

With returned reference to FIGS. 1A and 1B, the drive feature 31 of the cutting element 30 of a tissue resector 10 may comprise a wire (e.g., similar to a guide wire, etc.) of a known type and configuration. Without limitation, the drive feature 31 may comprise or consist of a solid filament. Alternatively, the cutting element 30 may include a coiled filament, which may surround a solid filament. Such a drive feature 31 may have any of a variety of suitable cross-sectional shapes; for example, round (e.g., circular, elliptical, oval, etc.), polygonal (e.g., triangular, rectangular, hexagonal, etc.), a flattened shape, or the like. Optionally, the drive feature 31 may include features that facilitate engagement and/or cutting of tissue, such as grooves or teeth that engage tissue or teeth or a sharpened edge that cuts into tissue. In still another alternative, the drive feature 31 may include proximal features (e.g., helical grooves, teeth, a helical thread, etc.) that facilitate the proximal movement of tissues through the lumen 24 of the cannula 20 of a tissue resector 10, for example, by breaking down tissues and other materials as they move proximally through the lumen 24, by forcing larger pieces proximally through the lumen 24 or by any other suitable mechanism.

FIGS. 4A through 4F depict a few non-limiting embodiments of cutting features 37 of cutting elements 30 that may be used in a tissue resector 10 (FIGS. 1A and 1B) according to this disclosure.

Figure 4A:
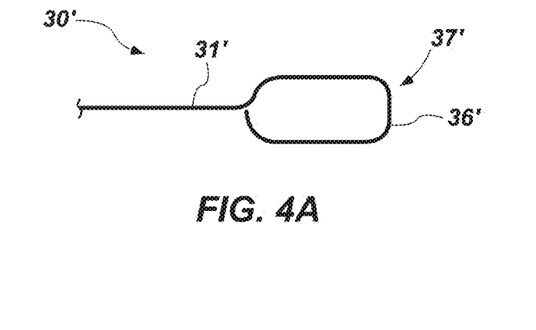
FIGS. 4A through 4F show some embodiments of cutting features that may be used with a tissue resector, such as that depicted by FIGS. 1A and 1B.

In FIG. 4A, an embodiment of a cutting element 30' is illustrated that is substantially linear along a majority of its length, with a cutting feature that comprises a cutting loop 37' at a distal end 36' of the drive feature 31' of the cutting element 30'. The cutting loop 37' of the cutting element 30' may be elongated. The length of the cutting loop 37' may be about the same as or exceed the length of an opening 27 (FIGS. 1A and 1B) of a cannula 20 (FIGS. 1A and 1B) with which the cutting element 30' is used. The width of the cutting loop 37' may be the same as, substantially the same as or less than the inner diameter of the lumen 24 (FIGS. 1A and 1B) of a cannula 20 (FIGS. 1A and 1B) with which the cutting element 30' is configured for use.

In use, both sides of an open cutting loop, such as the embodiment of cutting loop 37' depicted by FIG. 4A, may cut into and through tissue. Thus, a cutting element 30' with an open cutting loop (e.g., cutting loop 37', etc.) may cut tissue twice with each rotation.

Figure 4B:
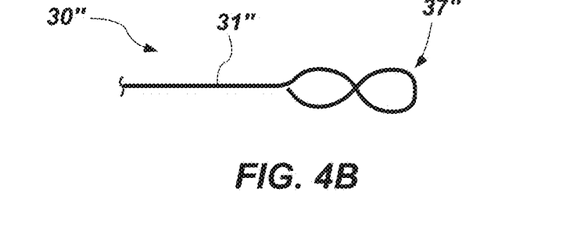

FIG. 4B illustrates an embodiment of cutting element 30" with a cutting feature that comprises a twisted cutting loop 37" at a distal end 36" of a drive feature 31" of the cutting element 30". As shown, a twisted cutting loop 37" may have a single twist, imparting it with a configuration that resembles a three-dimensional figure eight. Of course, a cutting loop 37" may have fewer than one twist or it may include more than one twist. The diameter of a twisted loop 37" may be the same as, substantially the same as or less than the inner diameter of the lumen 24 (FIGS. 1A and 1B) of a cannula 20 (FIGS. 1A and 1B) with which the cutting element 30" is configured for use. A twisted cutting loop 37" may comprise an open loop, or it may comprise a solid, flat element having a helical configuration.

Figure 4C:
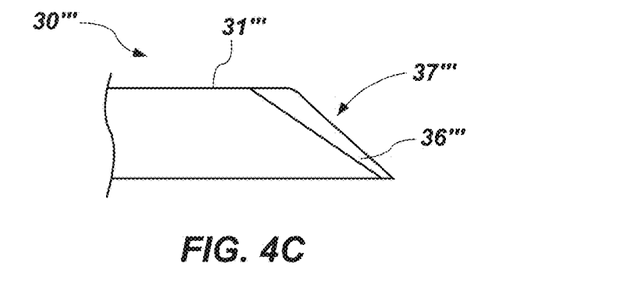

As another option, a cutting element 30''' may have a cutting feature 37''' formed in a distal end 36''' of a drive feature 31''' of the cutting element 30''', as illustrated by FIG. 4C. The cutting feature 37''' may comprise one or more sharp points, edges, indentations or other features that may enable it to engage and cut tissue.

Figure 4D:
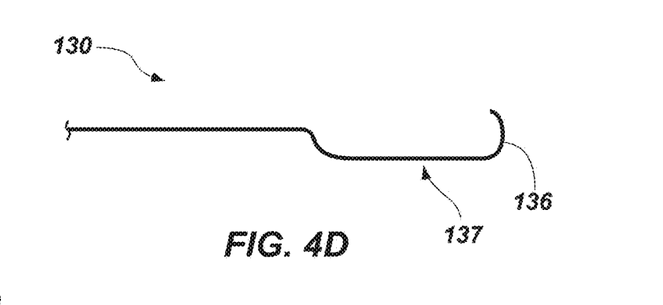

Another embodiment of cutting element 130 is shown in FIG. 4D. That cutting element 130 includes a cutting feature 137 located near a distal end 136 of the drive feature 131 of that cutting element 130. The cutting feature 137 comprises an elongated region of the drive feature 131 that is offset from a remainder of the length of the drive feature 131. The distance of the offset may be the same as, substantially the same as, or less than the radius of a lumen 24 (FIGS. 1A and 1B) of a cannula 20 (FIGS. 1A and 1B) within which the cutting element 130 is configured to be positioned. The distal end 136 of such a cutting element 130 may be configured to facilitate smooth rotation of the cutting element 137 relative to an opening 27 (FIGS. 1A and 1B) through a wall 22 of the cannula 20 with which the cutting element 130 is configured to be used. In the depicted embodiment, the distal end 136 of the cutting element 130 is configured complementary to the distal end 26 (FIGS. 1A and 1B) of the cannula 20.

Figure 4E:
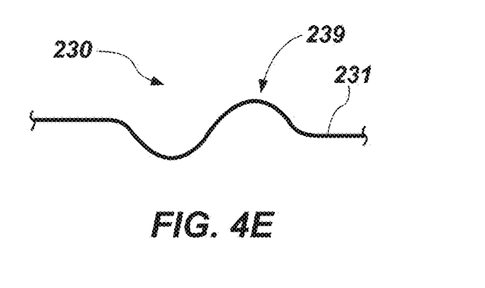

FIG. 4E illustrates an embodiment of cutting element 230 with a centering feature 239 along at least a portion of a length of a drive feature 231 of the cutting element 230, at a location proximal to a cutting feature (not shown) of the cutting element 230. The illustrated embodiment of centering feature 239, or any equivalently configured centering feature 239, may align an axis of rotation (not shown) of the cutting feature (not shown) with a longitudinal axis through the center of the lumen 24 (FIGS. 1A and 1B) of a cannula 20 (FIGS. 1A and 1B) with which the cutting element 230 is to be used. Such a configuration may optimize the stability with which the cutting element 230 rotates, providing for smooth rotation of the cutting element 230 within the lumen 24 of the cannula 20.

Figure 4F:
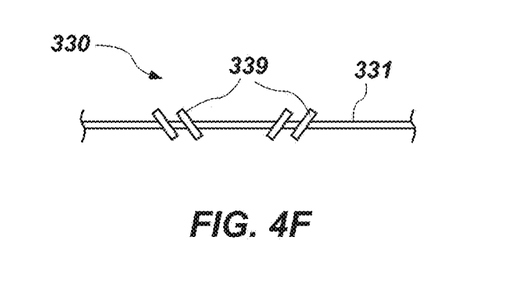

Another embodiment of cutting element 330 is shown in FIG. 4F. That cutting element 330 includes augers 339 along at least a portion of a length of a drive feature 331 of the cutting element 330. The augers 339 may be configured and oriented to facilitate the flow of excised tissue proximally through the lumen 24 (FIGS. 1A and 1B) of a cannula 20 (FIGS. 1A and 1B) with which the cutting element 330 is used. In some embodiments, at least some of the augers 339 may be configured and/or oriented to break the excised tissue into smaller pieces, further facilitating the rate at which they may flow proximally through the lumen 24 of the cannula 20. In some embodiments may comprise discrete elements. In other embodiments, the augers 339 may have helical configurations, which may comprise one or more Archimedes screws positioned along the length of the cutting element 330.

Figure 5A:
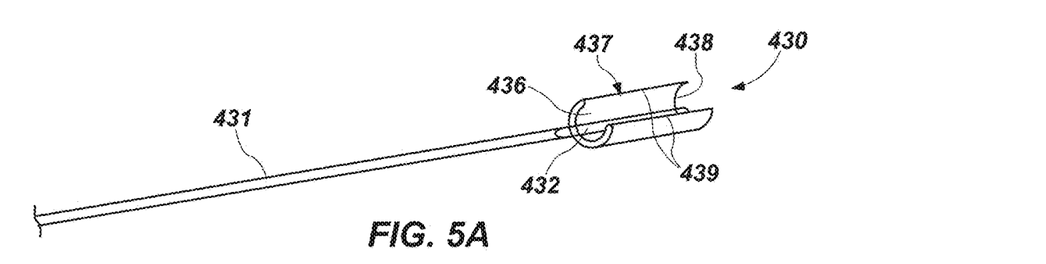
FIG. 5A depicts an embodiment of a cutting element with a semi-cylindrical cutting feature on a distal end of a drive feature that comprises a wire.

FIG. 5A illustrates an embodiment of cutting element 430 that includes an elongated drive feature 431 with a flattened distal end 432 and a cutting feature 437 secured to the flattened distal end 432. The cutting feature 437 may comprise a hollow, semi-cylindrical element with an open proximal end 436, into which the flattened distal end 432 of the drive feature 431 extends. A distal end 438 of the cutting feature 437 may also be open (e.g., to enable samples and/or debris to be aspirated therein, etc.). The cutting feature 437 may also include one or more features that may cooperate with an opening 27 through a cannula 20 (see, e.g., FIG. 1B). Opposed edges 439 of the cutting feature 437 may be capable of cutting into body tissue or other materials as the drive feature 431 is rotated within a lumen 21 of a cannula 20 of a tissue resector 10. In some embodiments, the edges 439 of the cutting feature 437 may comprise blades, teeth or serrations or other features that enable them to cut readily into and through body tissue or other materials.

Figure 5B:
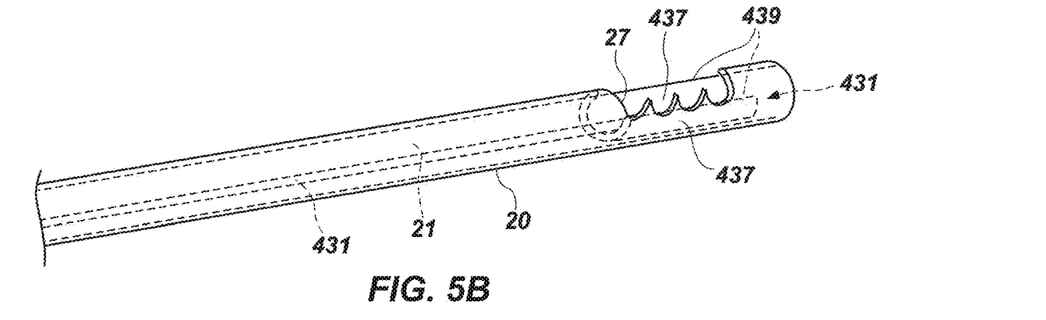
FIGS. 5B and 5D show an embodiment of a tissue resector that includes the embodiment of cutting element depicted by FIG. 5A.
Figure 5C:
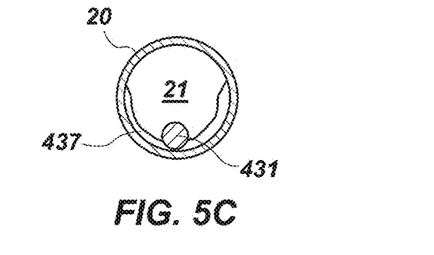
FIGS. 5C and 5E are cross-sectional views taken through intermediate locations of the tissue resectors in the arrangements depicted by FIGS. 5B and 5D, respectively.
Figure 5D:
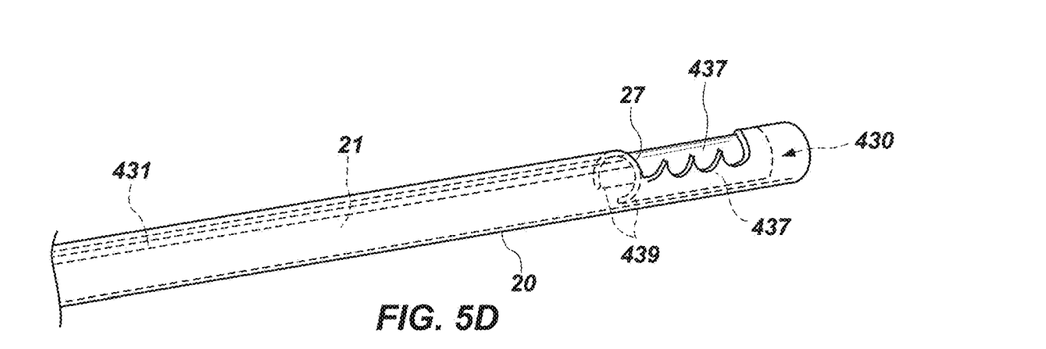
Figure 5E:
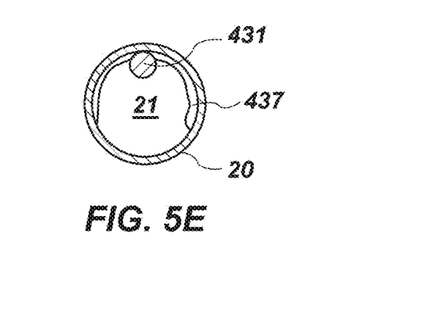
Figure 6A:
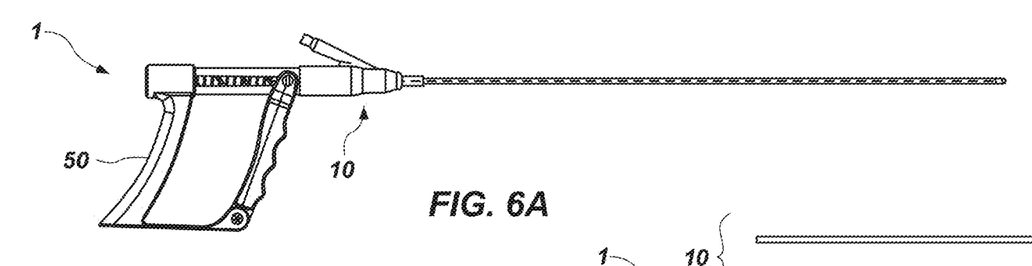
FIGS. 6A through 6C illustrate an embodiment of a tissue resector system that includes a tissue resector of the type shown in FIGS. 1A and 1B, as well as a hand-powered rooter, with FIG. 6A illustrating the tissue resector system in an assembled state, FIG. 6B providing an exploded view of the elements of the hand-powered rooter and the tissue resector and FIG. 6C providing a cross-sectional representation of the tissue resector system.
Figure 6B:
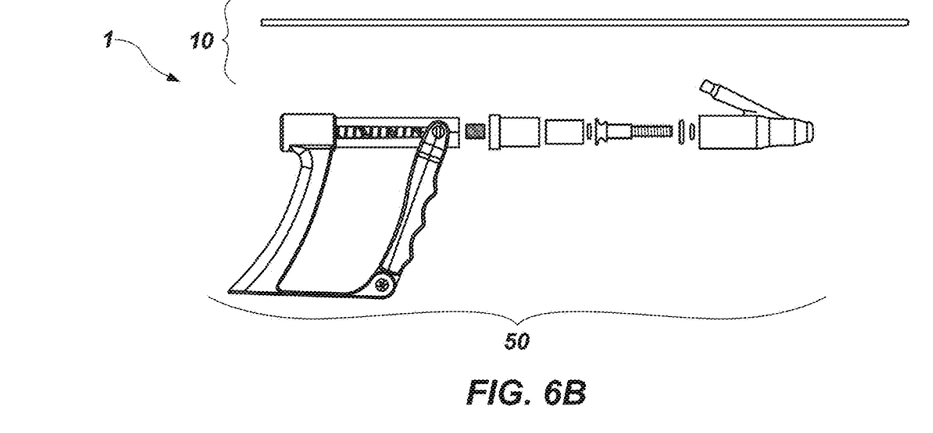
Figure 6C:
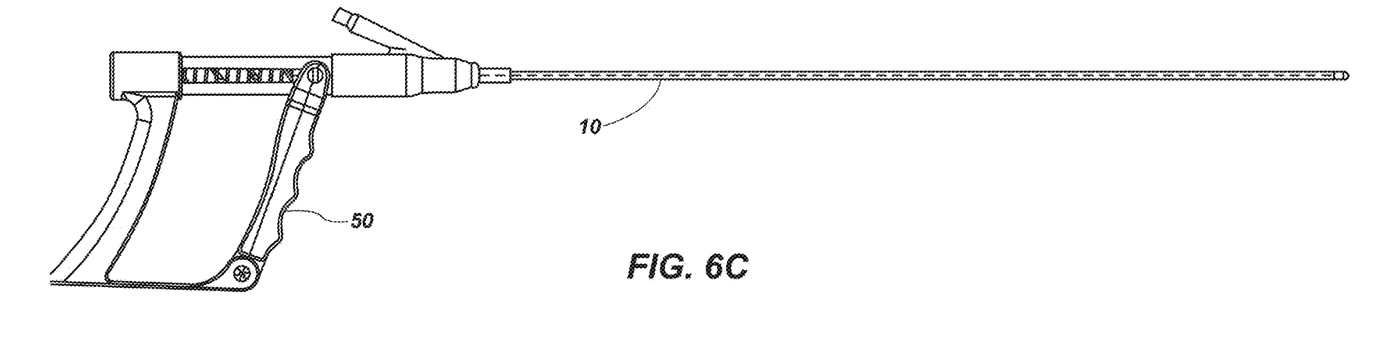

FIGS. 5B-5E depict different rotational orientations of the cutting feature 437 within the lumen 21 of the cannula 20 and, thus, different rotation rotational orientations of the cutting feature 437 relative to the opening 27 of the cannula 20. FIGS. 5B and 5C show the cutting feature 437 in an open orientation relative to the opening 27 of the cannula 20, with the opposed edges 439 of the cutting feature 437 oriented toward edges of the opening 27, such that an interior of the cutting feature 437 is open to the opening 27. FIGS. 5D and 5E show the cutting feature in a close orientation relative to the opening 27 of the cannula 20, with the opposed edges 439 of the cutting feature 437 oriented away from the edges of the opening 27, such that an outer surface of the cutting feature 437 is exposed through the opening 27.

Returning reference again to FIGS. 1A and 1B, a cutting feature 37 of a cutting element 30 of a tissue resector 10 according to this disclosure may have a length that exceeds a length of the opening 27 of the cannula 20 of the tissue resector 10. Such a configuration may improve the stability with which the cutting element 30 rotates within the lumen 21 of the cannula 20 and, thus, the stability with which the tissue resector 10 cuts tissue. Additionally, such a configuration may serve as a safety measure by preventing a cutting feature 37 that has been removed from the drive feature 31 of a cutting element 30 (e.g., by breaking off of the drive feature 31, etc.) from coming out of the opening 27 and entering a subject's body; a cutting feature 37 that has been removed from its drive feature 31 may remain trapped within the lumen 21 of the cannula 20.

The cutting element 30 of a tissue resector 10 may be of any suitable size (e.g., have an outer diameter) that will cut tissue in the desired manner while enabling the tissue to be aspirated through the lumen 24 of the cannula 20 at an acceptable rate (e.g., at a rate that will minimize the duration of a tissue resection procedure and, thus, the pain suffered by a patient, etc.). As an example, acceptable rates of aspiration may be achieved with a tissue resector 10 that has a lumen 24 with an open cross-sectional area (i.e., the cross-sectional area of the lumen 24 minus the cross-sectional area of the cutting element 30) that is at least 50% of the cross-sectional area of the cannula 20. In a specific embodiment, a cannula 20 with an outer diameter of 0.115 inch (i.e., a cross-sectional area of 0.0104 in$^2$) and an inner diameter of 0.095 inch (i.e., a cross-sectional area of 0.00709 in$^2$), when used with a 0.040 inch (i.e., 0.00126 in$^2$ in cross-sectional area) cutting element 30, will have an open cross-sectional area of 0.00583 in$^2$, which accounts for 56.1% of the entire cross-sectional area occupied by the cannula 20. Of course, the use of smaller cutting elements 30 would provide an even larger percentage of open area (e.g., at least 60%, at least 65%, at least 70%, etc.) and enable even greater rates of aspiration.

As depicted by FIG. 1B, at least a portion (e.g., at least a proximal portion, etc.) of the drive feature 31 of the cutting element 30 may be positioned within the lumen 21 of the cannula 20 along or substantially along, a central axis along a length of the cannula 20. In some embodiments, an entirety of the length of the drive feature 31 may be centrally located. In other embodiments, such a drive feature 31 may be bent at a distal location along its length to enable some embodiments of cutting features 37 to rotate adjacent to an inner surface of the lumen 21 of the cannula 20.

Alternatively, as illustrated by FIGS. 5B-5E, at least a portion (e.g., at least a proximal portion, etc.) of the drive feature 431 of the cutting element 430 may rotate eccentrically. The eccentric rotation of such a drive feature 431 position the drive feature 431 in close proximity to or even against an inner surface of the lumen 21 of the cannula 20. In some embodiments, the drive feature 431 may be linear or substantially linear, enabling an entirety of the drive feature 431 to reside at a common radial position along a length of the cannula 20. In other embodiments, the drive feature 431 may include one or more bends, enabling one portion of the drive feature 431 to rotate eccentrically, while enabling another portion of the drive feature 431 to rotate centrically or with another eccentricity, depending upon the offset distance defined by each bend. In a specific embodiment of such a drive feature 431, a first portion of the drive feature may be located at a first radial position within the lumen 21 of the cannula 20, while a second portion of the drive feature may be located at a different, second radial position within the lumen 21 of the cannula 20 (e.g., the first and second radial positions may be diametrically opposed, etc.). As at least a portion of the drive feature 431 rotates eccentrically, it may agitate tissue and/or debris within the lumen 21 of the cannula 20 and sweep tissue and/or debris from the inner surface of the lumen 21 of the cannula 20, both which may facilitate movement of tissue and debris proximally through the cannula 20.

As illustrated by FIGS. 5A through 5C, a tissue resector 10 according to this disclosure may be operated under manual power (i.e., by hand) with a rooter 50, such as that described by U.S. Patent Application Publication No. US 2012/0239008 of Fojtik. Together, the tissue resector 10 and the rooter 50 may provide a tissue resector system 1. Such a rooter 50 may easily be used to rotate a cutting element 30 at about 500 revolutions per minute (rpm), and can generate up to about 3,000 rpm, which may result in about 1,000 cuts per minute and 6,000 cuts per minute, respectively.

The rooter 50 of a tissue resector system 1 may enable rotation of a cutting element 30 of the tissue resector 10 as the cannula 20 of the tissue resector 10 is held substantially stationary. As the rooter 50 is manually operated, it may spin the cutting element 30 in a repetitious back-and-forth (i.e., clockwise and counterclockwise) manner, which may provide for two sets of cutting element 30 rotations with each pull (or push) on an actuator of the rooter 50.

Use of such a rooter 50 with the embodiment of the tissue resector 10 shown in FIGS. 5A-5E and described in reference thereto has been shown to remove tissue at much greater rates than the rates with which existing devices remove tissue. For example, based solely upon the time needed to complete the procedure (i.e., excluding any time needed to activate an electromechanically operated tissue resector), a 9 Fr (3.0 mm) resector 10 according to this disclosure, when rotated with a rooter 50, removed uterine polyps at a rate of 2.28 grams per minute (g/min), whereas the 9 Fr (3.0 mm) MyoSure Lite only removed uterine polyps at a rate of 1.6 g/min. A 5 Fr (1.65 mm) embodiment of the tissue resector 10 shown in FIGS. 5A-5E, when used with a rooter 50 of the type shown in FIG. 7 removed uterine polyps at a rate of 0.56 g/min, whereas a 9 Fr (2.9 mm) TruClear Incisor removed uterine polyps at a rate of only 0.29 g/min. Since a manually operated rooter 50 does not require the obligatory activation time of an electromechanical drive element, the rates at which a tissue resection system that includes a rooter 50 removes tissue are significantly greater than the above-mentioned electromechanically operated tissue resection systems.

When an embodiment of cutting element 30' (FIG. 4A) having an open cutting loop 37' (FIG. 4A) is used in the tissue resector system 1, since the cutting loop 37' cuts tissue twice with each rotation of the cutting element 30', manual operation of the rooter 50 and, thus, hand-operated rotation of the cutting element 30' may efficiently cut tissue and, thus, remove the same from an individual's body.

A rooter 50 that is configured for hand-powered operation may also be used with the limited use (e.g. disposable, etc.) portion 70 of a conventional morcellator, providing another embodiment of tissue resector system 1'.

Figure 7:
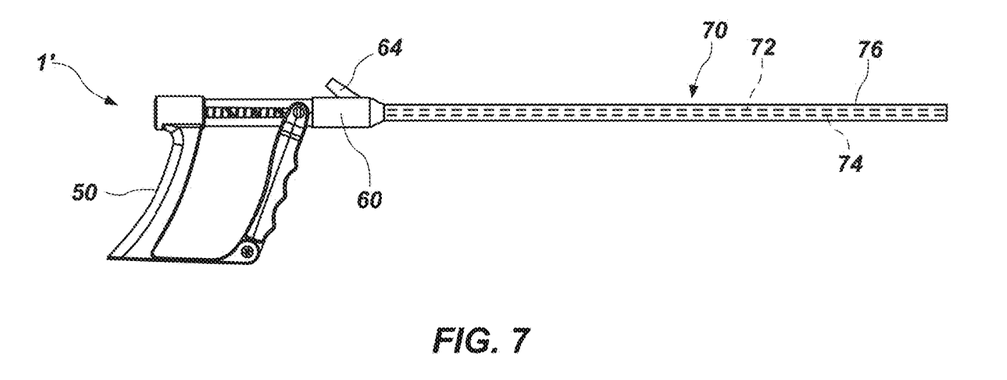
FIG. 7 shows an embodiment of an adapter for enabling use a hand-powered rooter with an existing morcellator, as well as an embodiment of a tissue resector system that includes the hand-powered rooter, the adapter and the morcellator.

The depicted embodiment of adapter 60 includes a series of elements that translate the action generated by the rooter 50 to an action that rotates the inner cannula, or blade 72, of a conventional morcellator. More specifically, the adapter 60 may include elements 61 and 62 that are respectively configured to engage a rotatable element of the rooter 50 and a proximal end 73 of the blade 72. Element 62, which is configured to engage the proximal end 73 of the blade 72, may be configured to rotate the blade 72 about an eccentric axis (e.g., an axis that enables the blade 72 to move rotational over an inner circumference of a lumen 74 of an outer cannula 76, etc.).

In addition, the adapter 60 may include one or more stationary elements 63 and/or a distal end cap 66 that may be configured to hold the outer cannula 76 that surrounds the blade 72 stationary, even while the blade 72 is rotated within a lumen 74 of the outer cannula 76.

In addition, the adapter 60 may include seals 67, 68, which enable movement of the blade 72 within the lumen 74 of the outer cannula 76. while simultaneously enabling the aspiration of body tissues, fluids or the like through the lumen 74 of the outer cannula 76, through the housing 65 of the adapter 60 and through an aspiration port 64 that communicates with an interior of the housing 65 of the adapter 60. Thus, the seals 67, 68 enable a suction (i.e., a vacuum) to be applied to the aspiration port 64 and communicated through the housing 65 of the adapter to the lumen 74 of the outer cannula 76 to drawn tissue, fluid or other materials proximally therethrough.

Figure 8:
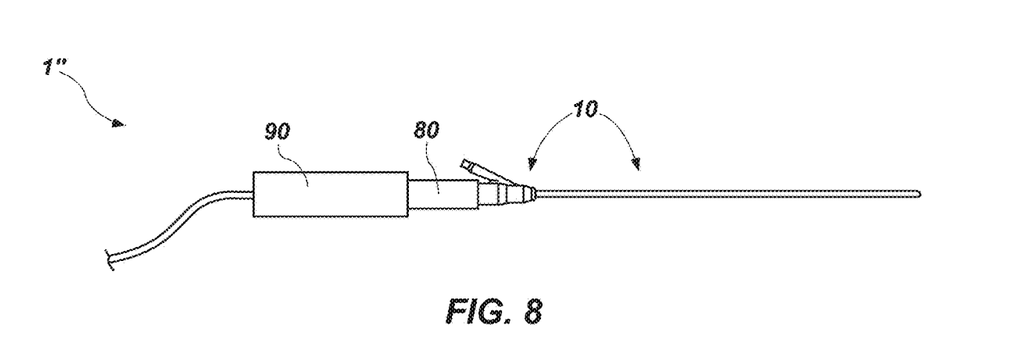
FIG. 8 depicts an embodiment of an adapter for enabling use of a tissue resector of the type illustrated by FIGS. 1A and 1B with a power-drive instrument of a conventional morcellation device, as well as an embodiment of a tissue resector system including the power-drive instrument, the adapter and the morcellator.

As depicted by FIG. 8, in another embodiment of tissue resector system 1", a tissue resector 10 may also be used with a power-drive instrument 90 of a conventional morcellator when coupled to the power-drive instrument 90 with an appropriately configured adapter 80. The adapter 80 may be configured to translate rotating action by the power-drive instrument 90 to the cutting element 30 (FIGS. 1A and 1B) of the tissue resector 10 and convert a system that aspirates through the power-drive instrument 90 for communication with the lumen 24 (FIGS. 1A and 1B) that extends through the outer cannula 20 (FIGS. 1A and 1B) of the tissue resector 10.

With returned reference to FIG. 7, in use, a tissue resector 10 may be secured to a rooter 50 by coupling the collar 60 of the cannula 20 to a proximal tip of the rooter 50 (e.g., rotatably coupling the collar 60 to the proximal tip of the rooter 50, etc.). An outflow port 64 of the tissue resector 10 may be secured to suction tubing. The resulting tissue resector system may then be operated by positioning an opening 27 of the cannula 20 and, thus, a cutting feature 37 of a cutting element 30 within the cannula, against a tissue that is to be resected, or removed. A trigger of the rooter may be squeezed with an individual's index finger and middle finger. A test squeeze may be performed first. The trigger of the rooter 50 may then be squeezed slightly (e.g., pulled back 1 cm to 2 cm, etc.) to open the opening 27 of the cannula (FIGS. 5B and 5C). With suction transmitted through the lumen 21 of the cannula 20, the tissue to be removed may be drawn into the opening 27 and between the edges 439 (FIG. 5B) of the cutting feature 437 of the cutting element 430. The trigger of the rooter 50 may be squeezed two or three times to cut the tissue. With each squeeze of the trigger, the cutting feature 473 rotates a plurality of times. The tissue that has been resected is then aspirated through the lumen of the cannula 20 and proximally out of the tissue resector 10. The opening 27 of the cannula 20 of the tissue resector 10 may then be repositioned and reused, as needed or desired.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A tissue resector, comprising:
   a cannula including:
      a wall;
      a lumen defined through the wall and extending along a length of the cannula;
      a distal end; and
      an opening at or adjacent to the distal end and establishing communication between an exterior of the wall and the lumen; and
   an elongated drive wire disposed within the lumen, the elongated drive wire being secured to a cylindrical cutting blade that cooperates with the opening through the cannula;
   wherein the elongated drive wire is configured to rotate eccentrically within the lumen;
   wherein the cylindrical cutting blade extends distal of the opening.

2. The tissue resector of claim 1, wherein an open cross-sectional area including a cross-sectional area of the lumen less a cross-sectional area of the elongated drive wire comprises at least 50% of the cross-sectional area of the cannula.

3. The tissue resector of claim 2, wherein the open cross-sectional area comprises at least 60% of the cross-sectional area of the cannula.

4. The tissue resector of claim 2, wherein the open cross-sectional area comprises at least 70% of the cross-sectional area of the cannula.

5. The tissue resector of claim 2, wherein an outer diameter of the cannula is about 0.115 inch and a diameter of the lumen is about 0.095 inch.

6. The tissue resector of claim 5, wherein the elongated drive wire has an outer diameter of about 0.040 inch or less.

7. The tissue resector of claim 1, wherein the opening of the cannula is defined through a circumference of the cannula.

8. The tissue resector of claim 7, wherein the opening of the cannula is spaced proximally from the distal end of the cannula.

9. The tissue resector of claim 7, wherein the opening of the cannula extends to the distal end of the cannula.

10. The tissue resector of claim 1, wherein the opening of the cannula is defined through the distal end of the cannula.

11. The tissue resector of claim 1, wherein the cannula further includes:
    at least one secondary opening through the wall of the cannula and located proximal to the opening.

12. The tissue resector of claim 1, wherein the opening of the cannula includes at least one edge configured to cut into tissue.

13. The tissue resector of claim 1, wherein the cylindrical cutting blade includes at least one edge configured to cut into tissue.

14. The tissue resector of claim 1, wherein the cylindrical cutting blade includes a central axis offset from a rotational axis of the elongated drive wire.

15. A tissue resection system, comprising:
    a tissue resector according to claim 1; and
    a hand-powered rooter for manually rotating the elongated drive wire of the tissue resector.

16. A tissue resection system, comprising:
    a tissue resector according to claim 1;
    a hand-powered rooter; and
    an adapter for translating an action of the hand-powered rooter to the elongated drive wire of the tissue resector to rotate the elongated drive wire.

17. A tissue resector system, comprising:
    a tissue resector according to claim 1;
    a power-driven instrument; and
    an adapter for translating an action of the power-driven instrument to the elongated drive wire of the tissue resector to rotate the elongated drive wire.

* * * * *